(12) United States Patent
McCann

(10) Patent No.: US 11,877,971 B2
(45) Date of Patent: Jan. 23, 2024

(54) BILATERAL COMPRESSION DEVICE

(71) Applicant: John McCann, Sandy, UT (US)

(72) Inventor: John McCann, Sandy, UT (US)

( * ) Notice: Subject to any disclaimer, the term of this patent is extended or adjusted under 35 U.S.C. 154(b) by 535 days.

(21) Appl. No.: 16/511,192

(22) Filed: Jul. 15, 2019

(65) Prior Publication Data

US 2019/0336377 A1    Nov. 7, 2019

(51) Int. Cl.
| | |
|---|---|
| *A61F 9/02* | (2006.01) |
| *A61F 13/12* | (2006.01) |
| *A61F 13/00* | (2006.01) |
| *A61H 1/00* | (2006.01) |
| *A61F 9/04* | (2006.01) |

(52) U.S. Cl.
CPC ............ *A61H 1/008* (2013.01); *A61F 9/026* (2013.01); *A61F 9/04* (2013.01); *A61F 13/00038* (2013.01); *A61F 13/124* (2013.01); *A61H 2205/025* (2013.01)

(58) Field of Classification Search
CPC .......... A61F 9/04; A61F 13/124; A61F 9/029; A61F 9/045; A61F 9/02; A61F 13/00029; A61F 13/122; A61F 2007/0004; A61F 2007/023; A61F 2009/021; A61F 5/3707; A61F 9/00772; A61F 9/028; A61F 9/026; A61F 13/00038; A61M 16/0616; A61M 16/0622; A61H 35/02; A61H 1/008
See application file for complete search history.

(56) References Cited

U.S. PATENT DOCUMENTS

| | | | | |
|---|---|---|---|---|
| 5,183,059 | A * | 2/1993 | Leonardi | A61F 9/04 128/858 |
| 5,879,292 | A * | 3/1999 | Sternberg | A61B 90/98 600/300 |
| 2006/0157064 | A1 * | 7/2006 | Davison | A61F 9/029 128/858 |
| 2012/0137414 | A1 * | 6/2012 | Saylor | B32B 27/00 2/435 |
| 2013/0025606 | A1 * | 1/2013 | de Juan, Jr. | A61F 9/0136 128/858 |

* cited by examiner

*Primary Examiner* — Ophelia A Hawthorne
(74) *Attorney, Agent, or Firm* — HOLLAND & HART LLP

(57) ABSTRACT

The present invention provides an improved bilateral compression device for post-operative surgical site, the bilateral compression device including a central cavity presented by an outerwall and a circumscribing sidewall, the central cavity in receipt of a post-operative pillow further comprising an outer membrane separated from an inner membrane for exerting a central compressive force towards the post-operative surgical area which varies from a surrounding compression force.

12 Claims, 5 Drawing Sheets

BILATERAL COMPRESSION DEVICE

CROSS-REFERENCES TO RELATED APPLICATIONS

This application is a continuation in part of and claims the benefit of U.S. non-provisional patent application Ser. No. 15/496,830, which was filed on Apr. 25, 2017.

FIELD OF THE INVENTION

The present invention is broadly directed to post operative treatment devices and, more particularly, to an improved post-operative bilateral compression device with contoured surfaces to reduce pain, diminish bruising, swelling and avoid fluid accumulation after ophthalmic procedures.

BACKGROUND OF THE INVENTION

Ophthalmological procedures general provide the most significant improvement in the quality of life. It is estimated that cosmetic eyelid surgery is the third most popular elective cosmetic procedure in the United States and it is anticipated that ophthalmology will experience the greatest growth in demand in the coming years based on an aging population and increased treatment success rates.

As a result of the increased number of surgical procedures, many people will experience the typical post-operative problems of swelling, pain and bruising which contribute to an extended healing period due to accumulation of fluids. Patients frequently complain about the bruising of the eyelids and the area surrounding the post-operative surgical area. Bruising of the eyelids may contribute to poor lid globe apposition which may lead to blurred vision and cause additional delays in the patient recovery.

In typical post-operative procedures, it is recommended to utilize the PRICE principals, namely to protect, rest, ice, compress and elevate around the affected areas to help them heal. However, the facial anatomy associated with typical ophthalmic surgical procedures presents unique difficulties which are effected by surrounding tissue, cartilage and bones which interfere with the PRICE techniques. In addition, maintaining compression and ice on the ophthalmic post-operative areas can create physical and psychological discomforts upon the treated patient.

For many years eyelid surgeons have recommended frequent ice compresses for the first few days after surgery to minimize bruising. Ice and cooling therapies generally help decrease blood loss, bruising, swelling, pain sensation and a general increase in the rate of recovery. However, the eyelids have a robust vascular supply and only a thin layer of skin to conceal bruising so that substantial bruising still occurs with heated and cooling therapies. In addition, the eye area is subject to swelling and "puffiness" which is part of a patients genetic predisposition, allergies, the aging process, lack of sleep, dietary considerations, and lifestyle considerations.

Because of the large vascular network around the eye, the eye area is subject to swelling which can increase during times of allergies, headaches, fatigue, edema, hangovers, environmental conditions, and medical and non-medical treatments including massages, botox, fillers and surgeries. It would therefore be beneficial to have a device for use during the post-operative process which helps reduce bruising of the eyelids and area surrounding the post-operative surgical area.

In the past, one solution has been to apply compressive eye patches post-operatively to the post-operative surgical area, e.g. the periocular area, with adhesive tape to help with recovery. However, eye patches are not acceptable for cases when both eyes are undergoing recovery for an extended period of time because they can create additional anxiety issues and physical limitations for the patient during the recovery process. Releasing patients to return home after surgery with taped-on compressive dressings over both eyes may lead to temporary blindness. This may result in greater chances of falls and other injuries which may be avoided if a removable compressive device was used while the patient is walking about and only worn while the patient is in the seated or supine position.

Normal, healthy ocular pressure is generally between 10 and 20 mm/Hg. Application of a some post-operative devices may increase or cause excessive ocular pressure (for example, pressure greater than 20 mm/Hg) which may cause discomfort, pain or may lead to temporary or permanent visual impairment or blindness. Eye patches are non-compliant and can contribute to the compartment syndrome which can lead to loss of vision in cases of retrobulbar hemorrhage. Therefore, there exits a need for an external compressive device which can apply compressive forces to the periocular area which is compliant and will not contribute to the compartment syndrome in cases of retrobulbar hemorrhaging.

Accordingly, there is a need for an improved post operative ophthalmologic device which is removable while providing desired bilateral compression as needed to assist the patient during the recovery period and addresses at least a portion of the aforementioned shortcomings.

SUMMARY OF THE INVENTION

The present invention includes an improved bilateral compression device for post-operative surgical site, the bilateral compression device including a central cavity presented by an outerwall and a circumscribing sidewall, said central cavity in receipt of a post-operative pillow further comprising an outer membrane separated from an inner membrane for exerting a central compressive force towards the post-operative surgical area which varies from a surrounding compression force. The device also conforms to the contour of the wearer and allows for various methods of adjusting the tension applied to the periocular area.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

DETAILED DESCRIPTION OF THE INVENTION

Figure 1:
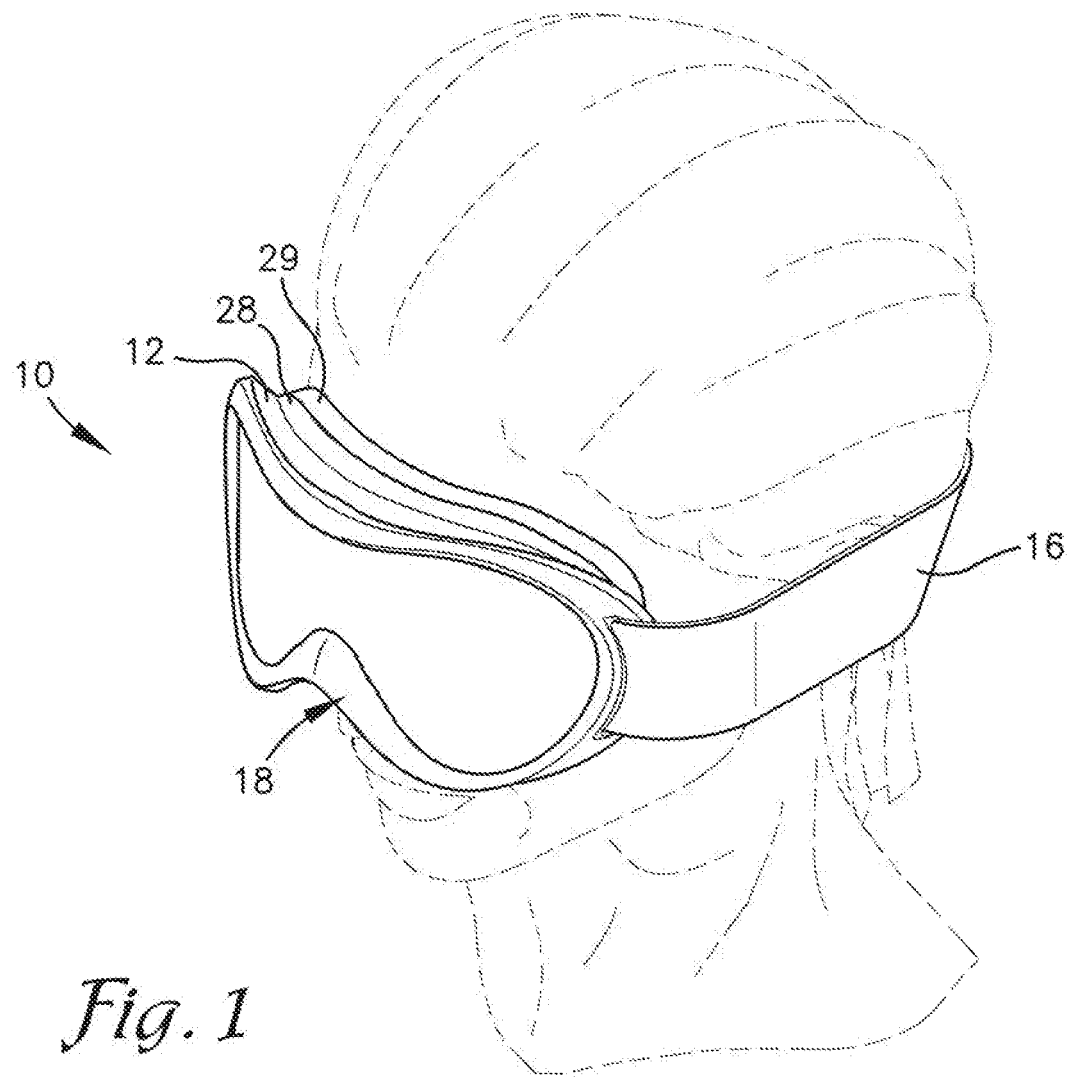
FIG. 1 is a left side perspective view of an exemplary embodiment of bilateral compression device.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 generally refers to an embodiment of the present invention, a bilateral compression device designed to be worn on the head of the patient after eye surgery to assist in the healing process. The bilateral compression device 10 includes a central cavity 20 presented by an outerwall 18 and a circumscribing sidewall 12 which generally extends along the outerwall 18.

Example materials which may be used for the outerwall 18 and circumscribing sidewall 12 include but are not limited to plastics and metals. In one embodiment, the outerwall 18 and circumscribing sidewall 12 may comprise a single rigid piece for example using an injection molding process. In one exemplary embodiment, the bilateral compression device 10 may utilize a goggle like one commercially available from Smith Optics, Inc. However, in an alternative embodiment, the outerwall 18 and circumscribing sidewall 12 may be flexible or fabricated as multiple pieces that can be selectively assembled and disassembled as desired. In yet another exemplary embodiment, the outerwall 18 and circumscribing sidewall 12 may be made from different materials, each having different properties and different shapes as desired.

The circumscribing sidewall 12 generally extends from the outerwall 18 providing a rim and in one embodiment may present a pair of slotted openings 14 which generally receive an elastic band 16, also referred to as a headband, for easy removal and adjustment of the bilateral compression device 10. Alternatively, the headband 16 may be attached to clips inserted through circumscribing sidewall 12. The elastic band 16 also allows the bilateral compression device 10 to remain on during the night while the patent sleeps. Generally, the elastic band 16 is provided that generally includes an elastic or resilient material to allow stretching of the elastic band 16 as desired for placement or removal of the bilateral compression device 10. Generally, the elastic band 16 with the outerwall 18 and circumscribing sidewall 12 presents a biased contoured surface for applying an even gentle pressure to the eyelids and the periocular region which is referred to generally as the post operative surgical site which includes the facial contours associated with the eyelids, eye socket and the nasal bone (not shown).

In some cases, the elastic band 16 may slide upward or downward on the back of the head which may result in elongation of the elastic band 16 and thus alter the pressure applied to the post operative surgical site associated with the bilateral compression device 10.

The bilateral compression device 10 generally outlines the periocular region associated with the post-operative surgical area with the circumscribing sidewall 12 extending along the outer area of the post-operative surgical area. In the depicted embodiment of FIG. 1, the circumscribing sidewall 12 extends along the outerwall 18 and presents a contact surface which extends around the optical socket and nose bridge area and may include a straight line, arc, polygon or irregular shape for extending along the post-operative surgical area. The tension on the elastic band 16 may be adjusted as desired for adjusting the compressive forces exerted by the bilateral compression device 10.

Generally, the central cavity 20 extends interiorly from the outerwall 18 outwardly along the circumscribing sidewall 12 and is adapted for receipt of a plurality of membranes. Alternatively, the central cavity 20 could include an area, at least partially extended exteriorly through the outerwall 18.

Figure 2:
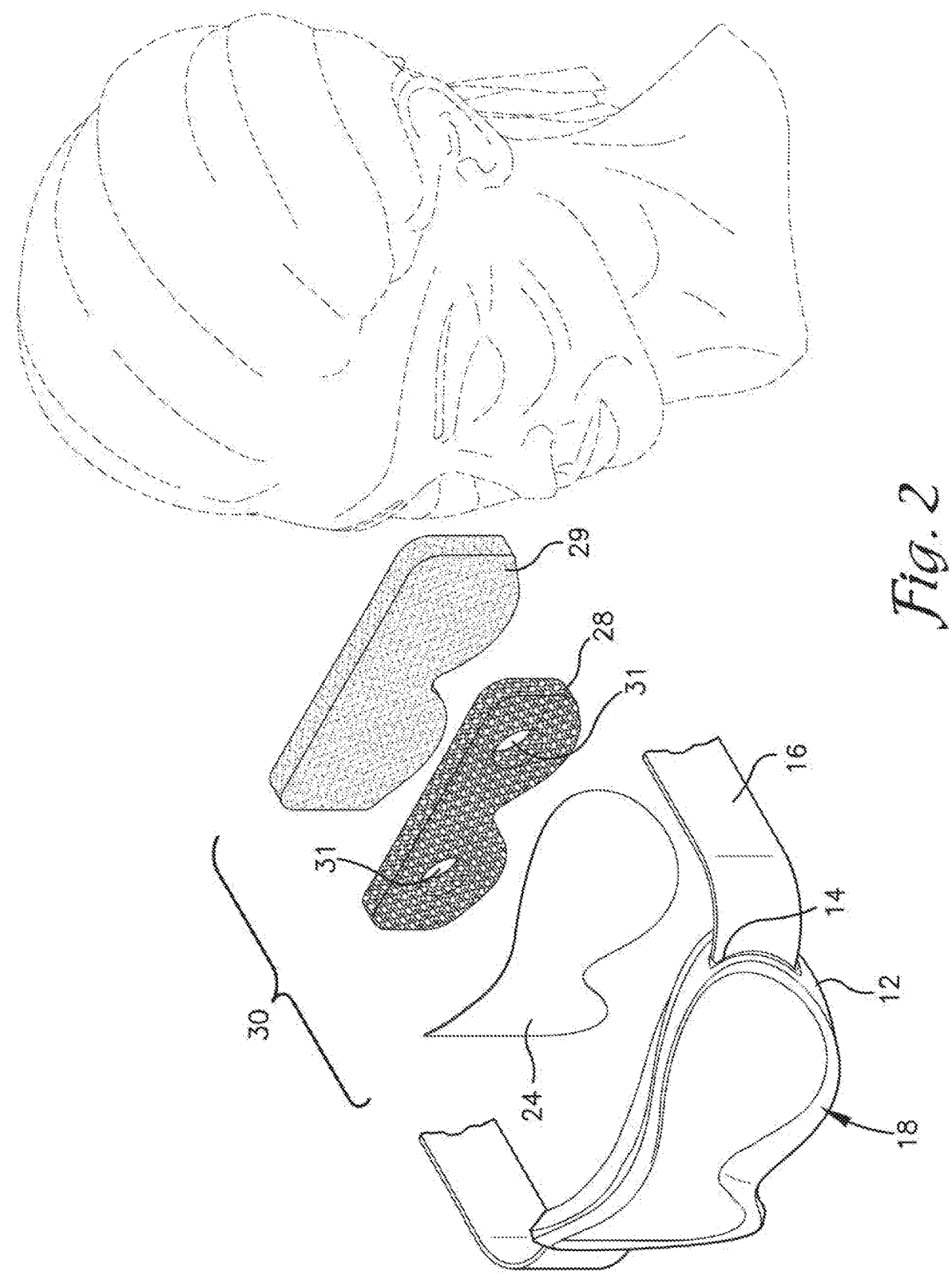
FIG. 2 is an exploded side perspective of the exemplary embodiment of FIG. 1.
Figure 3:
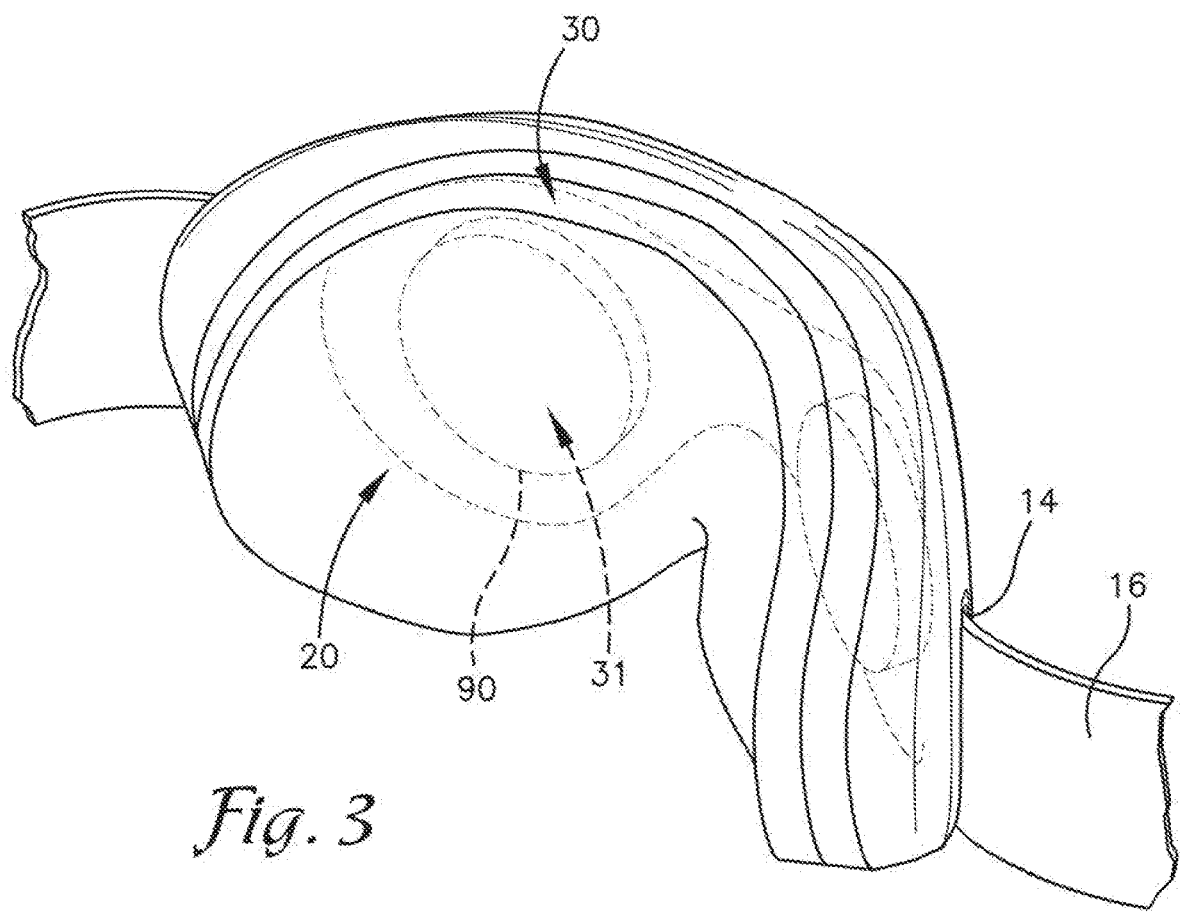
FIG. 3 is a rear perspective of the exemplary embodiment of FIG. 1.

An exemplary embodiment of a post-operative pillow 30 is depicted in FIG. 2 and includes an outer membrane 24 separated from an inner membrane 29 by a compression membrane 28. Generally, the recesses 31 having a shaped opening are formed by removing at least one central portion along each side of the compression membrane 28 facilitating communication through the compression membrane 28, between the compression membrane 28 and the inner membrane 29. In one embodiment, the recesses 31 are adapted for transmitting the central compressive forces therethrough. Additionally, and/or alternatively, the compression membrane 28 may be manufactured with a plurality of perforations 90 along the central portion of the inner membrane 29 allowing for the central portion to be removed easily. Once the central portion is removed, the light may enter through the central portion allowing for visual communication therethrough, reducing any pressure exerted by the central portion upon the surgical area. In some situations it may be beneficial to remove only one side of the central portion, where for example, it is desirable to apply pressure to one eye while allowing vision through the other eye.

Generally, the post-operative pillow 30 is configured for receipt by the central cavity 20. In operation, the post-operative pillow 30 provides multiple compressive forces upon the post-operative surgical area. In the depicted embodiment of FIG. 2, the post-operative pillow 30 provides a reduced compressive force along a central area 31 within said compression membrane 28 having a left and right side, also referred to as a pair of recesses. Generally, the compression membrane 28 has a greater compressive force extended outwardly from the opening associated with the recess 31 towards the facial area surrounding the post-operative surgical area, less force being applied along the recess 31 associated with the delicate facial area such as the area associated with the wearer's eyelid and globe tissue. While the embodiment depicted in FIG. 2 generally provides for a bilateral compression, or two different compression forces, additional compression forces may be utilized in the present invention as desired for selectively reducing the swelling and discomfort associated with the post-operative surgical area to assist in the healing process.

The compression forces exerted upon the post-operative surgical area by the bilateral compression device 10 generally correspond to the properties of the post-operative pillow 30. Generally, two compression forces are provided, a central compression force and a surrounding compression force. The central compression force corresponds to the recess 31, while the surrounding compressive force corresponds to the compression membrane 28. Thus the compression forces exerted upon the post-operative surgical area vary by the configured recess 31 and the selected compression membrane 28. Generally, the desired compression for the central compression force varies in pressure from the surrounding compression force. The recess 31 is configured to reduce the central compression force and limit any intraocular pressure increase and to allow the globe to move forward in the case of a post-operative orbital hemorrhage.

The outer membrane 24 is generally an opaque or translucent material which is configured for placement between the outerwall 18 and the central cavity 20. The outer membrane 24 may also provide a moisture barrier to prevent any unwanted condensation within the central cavity 20 during use. The outer membrane 24 depicted in FIG. 2, generally has a continuous layer which is adapted for placement on the outerwall 18 along the inner cavity 20 and for receiving the compression membrane 28. The outer membrane 24 may be secured with, for example, an additional adhesive layer (not shown) to the compression membrane 28. The adhesive layer may also be omitted, or otherwise modified as is known for securing the outer membrane 24 to the compression membrane 28.

The post-operative pillow 30 is configured for receipt within the central cavity 20 and generally provides for compression along the relevant facial contours such as the nose bridge, eyelid and/or eye-socket (not shown). In the depicted embodiment of FIG. 2, the post-operative pillow 30 generally includes the facial membrane 29 and the compression membrane 28. One embodiment of the compression membrane 28 includes utilization of a generally compressible cellular material which is compressible, moisture resistant and provides thermal insulation. The compressible cellular material associated with the compression membrane 28, when utilized, of FIG. 2 may be used either individually or in combination with different or additional material and either configured as a continuous layer or selectively positioned within the central cavity 20 to provide the desired protection and compressibility at the relevant post-operative location. By way of example, the material used for the compression membrane 28 may be, but is not limited to, a laminated cellular foam material which is moisture resistant and has a thickness of around ½" thick, but at least ¹⁄₁₆" thick. An example of commercially available material includes ENSOLITE styles IV1, IV2, IV3, IV4, IV5, GIC OR IVC all manufactured by Ensolite, Inc. of Mishawaka, Ind.

The compressible membrane 28, is configured for placement within the circumscribing sidewall 12 for receipt by the central cavity 20. Generally, the compression membrane 28 may be bonded directly to the outerwall 18 to help keep out moisture and maintain the interior temperature within the central cavity 20 during use.

The inner or facial membrane 29 is generally fabricated from a material designed to cushion the treated area of the patient body after the surgical procedure. During use, the facial membrane 29 may become dirty or soiled from use in connection with the post-operative treatment. Therefore, in one embodiment, the facial membrane 29 may be removed, with a new or fresh facial membrane 29 being applied to the post-operative pillow 30. The facial membrane 29 in the depicted embodiment, is substantially planar with a configuration which generally corresponds to the central cavity 20. The inner membrane 29 may be fabricated from a variety of compressible materials which are suitable for treating wounds but in a preferred situation, it would have a smooth, comfortable surface which would limit irritation or adhesion to the post-operative area. By way of example, and not as a limitation, the inner membrane 29 may be fabricated from a compressible polyurethane foam material with or without a silicon coating. Generally, the inner membrane 29 is breathable, flexible with a durable coating having excellent adhesion properties. In addition, it may include a phase-change water-based coating which may help it maintain an ideal comfortable temperature by acting as a heatsink, conducting heat away from the surface. Examples may include material made by Mentor Corporation under the trade name EPI-FOAM or TOPIFOAM. Another example may include material made by Bergad Specialty Foam under the trade name COOLCELL.

The inner membrane 29 may be secured to the compression membrane 28 or to the circumscribing sidewall 12 mechanically with, for example, silk or chemically with for example adhesive. At least a portion of the central portion of the inner membrane 29 may be removed and frictionally secured to the remainder of the surrounding inner membrane 29 to allow for visual communication through the central cavity 20, for example, to allow the patient to see through the compressive pillow on the side where a portion of the inner membrane 29 has been removed.

In another embodiment, the inner membrane 29 may be fabricated from foam with a covering on the side of the foam that touches the skin composed of a gel or graphite or some other material to allow heat to be carried away from the skin and/or to be cooled. It may be fabricated from a type of foam that has cooling properties independent of any coating such as that sold commercially under the trade name COOLCELL by Bergad Specialty Foams.

In one operational embodiment, the bilateral compression device 10 may be placed on the patient's head while the patient is laying back with the post-operative pillow 30 placed within the central cavity 20, the inner membrane 29 pressed against the facial contours around the post-operative surgical area (not shown). The inner membrane 29 extends across the upper and lower eye (not shown) with the post-operative pillow 30 exerting pressure across each eye region. The pressure may be adjusted with the elastic band 16, with for example a buckle (not shown) or another adjustment mechanism to reduce or increase the pressure as desired.

As previously indicated, the circumscribing sidewall 12 presents a contact surface which extends around the optical socket, eyelid and nose bridge area associated with the post-operative surgical area (not shown). The bilateral compression device 10 may be removed as desired and the inner membrane 29 may be removed or changed as needed. Alternatively, the inner membrane 29 may alternatively be configured to warm, cool or to help heal the post-operative surgical area such as by dispensing ointments, drops or other post-operative treatments upon the surrounding post-operative surgical area as desired through for example a use of a medicated dressing which has specially treated membranes which have various known substances impregnated into the material of the inner membrane 29.

Figure 4:
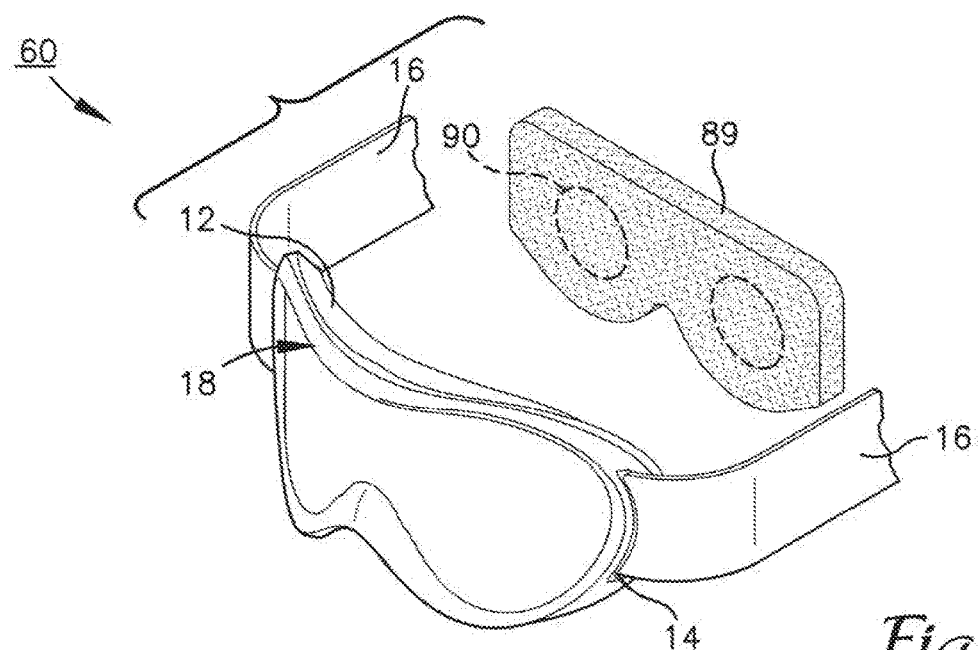
FIG. 4 is a side perspective of an alternative embodiment of the bilateral compression device.
Figure 5:
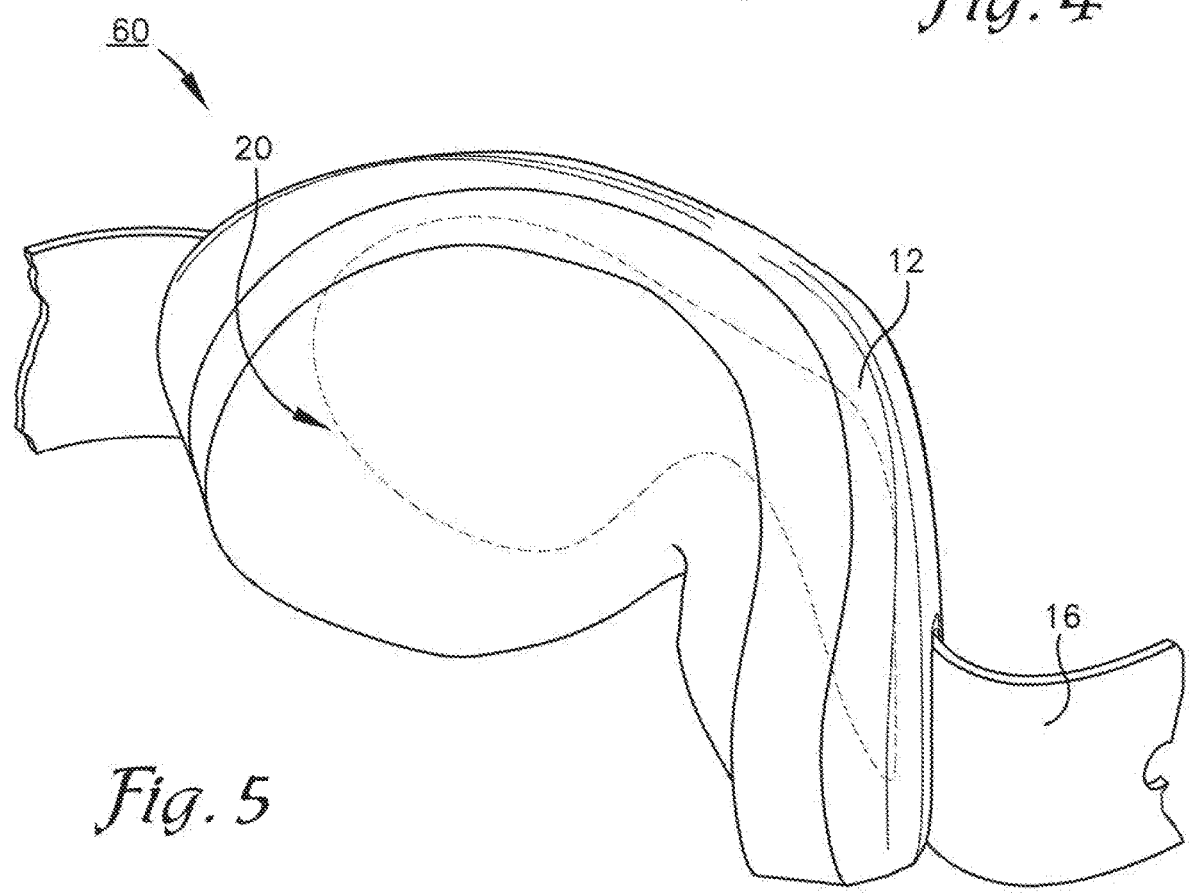
FIG. 5 is a rear perspective of the alternative embodiment of FIG. 4.

An alternative embodiment of the bilateral compression device 60 is illustrated in FIGS. 4-5 with central cavity 20 adapted for receipt of an alternative inner membrane 89 having optional perforations 90 for selective removal of a portion thereof for visual communication through the inner membrane 89. For example, the central portion associated with each of the left and right side of the inner membrane 89 may each be irregularly shaped or regularly shaped as presented by the plural perforations 90 spaced along the inner membrane 89 for selective removal of one or both of the left or right side central portion associated with the recesses 31 to allow for visual communication therethrough. In this way, the pressure for at least one side may be reduced or the wearer may be able to see through the inner membrane 89, the compression membrane 28 and outer membrane 24 during the day to help avoid various injuries.

Figure 6:
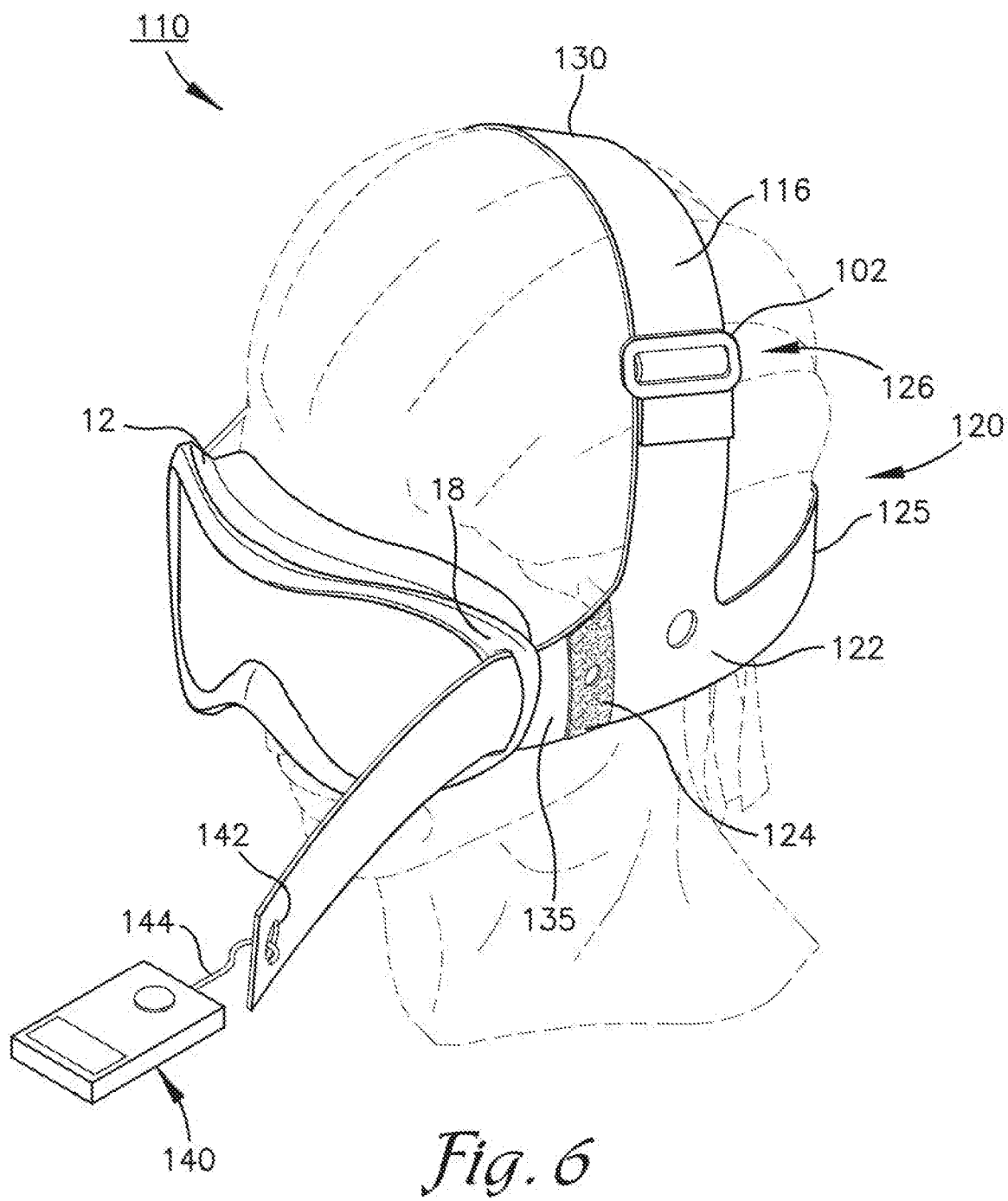
FIG. 6 is a side perspective of a second alternative embodiment of the bilateral compression device.

In another alternative embodiment of the bilateral compression device 110 illustrated in FIG. 6, a shaped headband 116 is provided which includes a rear support 120 which is designed to limit unwanted upward movement of the headband 116 during wear. Generally, the illustrated shaped headband 116 includes an adjustment member 102, an inferior portion 125, a superior portion 130 and an anterior projection 135 joined at a headband junction 122.

During wear, the inferior portion 125 extends rearwardly from the headband junction 122 to rest on the inferior edge of the occipital protuberance of the wearer's head. The inferior portion 125 generally provides posterior and downward bias for the bilateral compression device 110 which is at least partially offset by the superior portion 130 to stabilize the bilateral compression device 110 so that upward or downward movement on the back of the head is limited.

The superior portion 130 extends from the headband junction 122 vertically towards a vertex of the skull and provides vertical bias which at least partially vertically supports the bilateral compression device 110. The bias presented by the superior portion 130 at least partially offsets the downward bias presented by the inferior portion 125. The superior portion 130 and inferior portion 125 are joined to present a posterior opening 126 which when worn, encircles a portion of the occipital and parietal bone associated with the wearer's head.

The anterior projection 135 extends from the bilateral compression device 110 towards the headband junction 122 and is generally configured for receipt by slotted openings 14. The distal or anterior projection 135 attaches posteriorly to the headband junction 122 where the anterior, inferior and superior portions 135, 125, 130 intersect. The proximate posterior end of the anterior projection 135 is located opposite the headband junction 122 and near the bilateral compression device 110. In one embodiment, the anterior projection 135 is aligned with the slotted openings 14 using for example a fastener 124 such as a hook and loop fastener, which is easily adjusted during the initial configuration of the bilateral compression device 110 for wear by a user. By aligning the anterior projection 135 with the slotted openings 14, the tension on the anterior projection 135 can be easily adjusted and readily secured as desired for applying the selected compression upon the post operative surgical site. In one embodiment, the compression can be adjusted to a specific level using a compression measurement device or tool 140. In another embodiment, the compression can be adjusted by extending the anterior projection 135 to specific indicia as further described below.

As illustrated in FIG. 6, an optional compression measurement tool 140 may be utilized to configure the alternative bilateral compression device 110, the compression force being measured with, for example, a scale. The embodiment of the fastener 124 associated with the anterior projection 135 includes a readily adjustable hook and loop type fastener 124. In addition, a receiver 142 is located on the proximate end of the anterior projection 135 which is adapted for connected operation by the compression measurement tool 140. The receiver 142 may alternatively be associated with the outerwall 18 or sidewall 12.

The compression measurement tool 140 may be digital or mechanical. The illustrated compression measurement tool 140 also includes attaching means 144, like a hook or other fastening structures which can be easily secured to and removed from the receiver 142. In operation, the compression measurement tool 140 includes internal force measuring structure connected to a visual display which indicates an increase or decrease in compressive force through a mechanical connection to the anterior projection 135.

Alternatively, the proximate end of the anterior projection 135 may include a plurality of indicia spaced along the anterior projection where each successive indicia represents an increase in compression according to the well known Hooke's Law, where the end of the anterior projection is stretched or extended from an uncompressed position to the desired compressed position, the successive indicia on the anterior projection 135 representing the extension directly corresponding to the applied compressive force according to $F=k \times e$. The indicia (not shown) may be incremented to accommodate configuration of the bilateral compression device 110 for compression with users having varying dimensions, including varying head sizes.

Alternatively, plural pressure sensors (not shown) may be embedded within or along a surface of the alternative facial membrane 89 for aligning the tension on the shaped headband 116 to a desired pressure. The pressure sensors (not shown) may utilize wireless or wired communication technologies, including Bluetooth, for conveying the associated tension data as determined by the pressure sensor (not shown) at a location using for example a microprocessor. The conveyed data may be displayed graphically or numerically on a user device, such as a smartphone, and may include an over-limit or under-limit alarm or setting.

In an exemplary operation of the use of the compressive measurement tool 140, the anterior projection 135 is received by the slotted openings 14 and pulled forward. The compression measurement tool 140 is attached through the receiver 142 located on the proximate end of the anterior projection 135. The anterior projection 135 is then adjusted until the desired amount of compression is applied as indicated by the compression measurement tool 140 and then the anterior projection 135 is then secured to the shaped headband 116 to maintain the desired compression.

The anterior projection 135 upon the post-operative surgical site by the bilateral compression device 110 for proper adjustment of the tension applied to the bilateral compression device 10, 110 by the headband 16, 116.

Adjustment member 102 may be located on, near or between any of the anterior, inferior or superior portions 135, 125, 130 to allow for selected adjustment of the shaped headband 116 based in part on the desired comfort to accommodate various dimensions associated with a user. The shaped headband 116 may include a plurality of adjustment members 102 any one of which may be associated with one or more of the anterior, inferior or superior portions 135, 125, 130. Generally, the adjustment member 102 helps for adjusting the bias exerted by or upon the bilateral compression device 110 including the various vertical or horizontal components until the desired pressure is achieved.

Adjustment members 102 being generally known, may include, but are not limited to, various mechanical fasteners such as snaps, buttons, zippers and hook and loop fasteners. In addition, to adjustment of the bias, the length of at least one of the anterior, inferior or superior portions 135, 125, 130 may be adjusted as desired for proper placement of the alternative bilateral compression device 110, using for example buckle, hook and loop or other type of length adjustment member 102.

The anterior projection, inferior and superior portions 135, 125, 130 may independently or collectively be fabricated from an elastic or flexible material which is adjustable and presents the desired bias to the bilateral compression device 110 for adjusting the pressure exerted upon a periocular region associated with the post-operative surgical area.

It is to be understood that while certain forms of the present invention have been illustrated and described herein, it is not to be limited to the specific forms or arrangement of parts described and shown.

The invention claimed is:

1. A post-operative bilateral compression device comprising:
   a central cavity presented by an outerwall and a circumscribing sidewall, said circumscribing sidewall presenting a contoured surface;
   a band secured to said circumscribing sidewall for securing said post-operative bilateral compression device during use;
   a post-operative pillow received by said central cavity and configured to provide multiple compressive forces;
   a compression membrane configured to exert said multiple compressive forces and a recess presented by said post-operative pillow, said multiple compressive forces comprising a central compressive force and a surrounding compressive force;
   said recess configured to reduce said central compressive force such that said central compressive force is less than said surrounding compressive force; and
   said compression membrane associated with a surrounding compressive force which extends outwardly from said recess.

2. The post-operative bilateral compression device of claim 1 wherein said post-operative pillow further comprises an inner membrane separated by an outer membrane.

3. The post-operative bilateral compression device of claim 2 wherein said inner membrane presents a smooth, non-stick surface.

4. The post-operative bilateral compression device of claim 2 wherein said inner membrane has a coating.

5. The post-operative bilateral compression device of claim 2 further comprising a compression membrane positioned between said inner and outer membrane.

6. The post-operative bilateral compression device of claim 2 wherein said outer membrane provides visibility through said post-operative bilateral compression device.

7. The post-operative bilateral compression device of claim 2 wherein said inner membrane further comprising a left side and a right side wherein at least some of one of said left and right side is removable.

8. The post-operative bilateral compression device of claim 1
   wherein said band further comprises;
   an adjustment member with a plurality of spaced indicia;
   said indicia extending along an anterior projection; and
   a headband junction configured for joining said anterior projection to said adjustment member, wherein said indicia correspond to an applied compressive force, wherein at least one of said indicia corresponds to said central compressive force.

9. The post-operative bilateral compression device of claim 8 wherein said plurality of spaced indicia correspond to varying levels of compression during use.

10. The post-operative bilateral compression device of claim 1 wherein said circumscribing sidewall presents a sealing surface which extends along the post-operative surgical site.

11. The post-operative bilateral compression device of claim 1 wherein said band includes a receiver for receipt of a compression measurement tool for quantitative adjustment of said central compressive force.

12. A post-operative bilateral compression device comprising:
   a central cavity presented by an outerwall and a circumscribing sidewall, said circumscribing sidewall presenting a contoured surface;
   a band secured to said circumscribing sidewall for securing said post-operative bilateral compression device during use;
   said band secured by a headband junction to an adjustment member; said adjustment member comprising a plurality of spaced indicia extending along at least a portion of said band, wherein at least one of said indicia correspond to an applied compressive force;
   a post-operative pillow received by said central cavity and presenting at least a first and a second compressive force;
   said first compressive force associated with a recess; and
   said second compressive force associated with a compression membrane and extending outwardly from said recess along said compression membrane, said second compressive force being less than said first compressive force.

* * * * *